United States Patent [19]

Wilk

[11] Patent Number: 5,217,003
[45] Date of Patent: Jun. 8, 1993

[54] AUTOMATED SURGICAL SYSTEM AND APPARATUS

[76] Inventor: Peter J. Wilk, 185 West End Ave., New York, N.Y. 10023

[21] Appl. No.: 670,720

[22] Filed: Mar. 18, 1991

[51] Int. Cl.$^5$ ............................ A61B 1/00; A61B 1/06
[52] U.S. Cl. ............................................. 128/4; 128/6
[58] Field of Search ................................ 128/4, 6, 903

[56] References Cited

U.S. PATENT DOCUMENTS

| | | |
|---|---|---|
| 3,834,392 | 9/1974 | Lampman et al. ............... 128/4 X |
| 4,343,300 | 8/1982 | Hattori ................................. 128/6 |
| 4,499,895 | 2/1985 | Takayama .......................... 128/6 |
| 4,572,198 | 2/1986 | Codrington . |
| 4,573,452 | 3/1986 | Greenberg ........................ 128/20 |
| 4,621,618 | 11/1986 | Omagari ............................. 128/6 |
| 4,633,304 | 12/1986 | Nagasaki ....................... 128/903 X |
| 4,672,963 | 6/1987 | Barken . |
| 4,758,222 | 7/1988 | McCoy ............................ 128/6 X |
| 4,791,934 | 12/1988 | Brunnett . |
| 4,996,975 | 3/1991 | Nakamura ...................... 128/4 X |

FOREIGN PATENT DOCUMENTS

| | | | |
|---|---|---|---|
| 0079524 | 5/1983 | European Pat. Off. ................ 128/4 |
| 3431022 | 3/1985 | Fed. Rep. of Germany .......... 128/4 |

Primary Examiner—Gene Mancene
Assistant Examiner—Nicholas D. Lucchesi
Attorney, Agent, or Firm—R. Neil Sudol; Henry D. Coleman

[57] ABSTRACT

A surgical system comprises an endoscopic instrument, a camera on the endoscopic instrument for obtaining video images of internal body tissues inside a patient's body via the endoscopic instrument, and a transmitter operatively connected to the camera for transmitting, over a telecommunications link to a remote location beyond a range of direct manual contact with the patient's body, a video signal encoding the video image. A receiver is provided for receiving actuator control signals from the remote location via the telecommunications link. The receiver feeds the signals to a robot actuator mechanism for controlling that mechanism to operate a surgical instrument insertable into the patient's body.

20 Claims, 1 Drawing Sheet

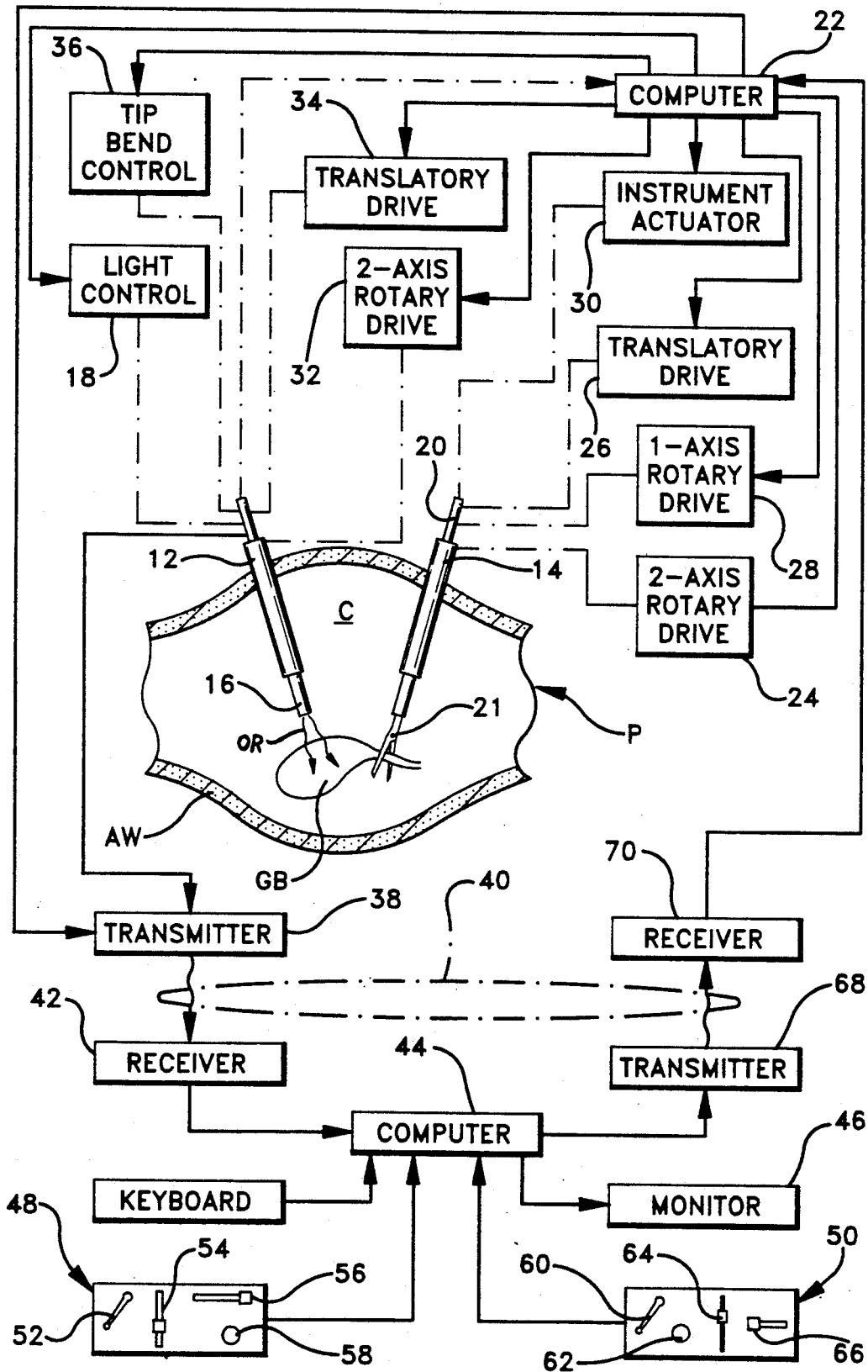

AUTOMATED SURGICAL SYSTEM AND APPARATUS

BACKGROUND OF THE INVENTION

This invention relates to a surgical system and a related method. More particularly, this invention relates to an endoscopic or laparoscopic surgical method and apparatus.

The advantages of laparoscopic and endoscopic surgical methods have become increasingly apparent to surgeons and to society at large. Such surgical techniques are minimally invasive, require less operating time, and reduce trauma and convalescence time required after surgery is completed. In general, noninvasive surgery using laparoscopic and endoscopic techniques will be used more and more frequently to reduce hospital and surgical costs.

In endoscopic and laparoscopic surgery, the surgeon is provided with visual information through optical fibers extending through the endoscope or laparoscope. Sometimes, the visual information is provided to the surgeon and other operating room personnel via video monitors which show images obtained by small video cameras (charge coupled devices) at the distal ends of the endoscopes or laparoscopes. Although this video information may be transmitted to other rooms in the hospital or other institutional clinical setting, the surgeon is always present in the operating room to manipulate the surgical instruments and thereby perform the surgical operation in response to the video images on a monitor.

The use of video images provides an opportunity for further reductions in the expense and time required for surgery.

OBJECTS OF THE INVENTION

An object of the present invention is to provide a method and apparatus for performing surgery which reduces surgical costs.

Another object of the present invention is to provide such a method and apparatus usable with endoscopic and/or laparoscopic equipment.

Another, more particular, object of the present invention is to provide a method and apparatus which facilitates the performance of operations by surgeons from all over the world.

SUMMARY OF THE INVENTION

A surgical method, in accordance with the present invention, comprises the steps of (a) inserting an endoscopic instrument into a patient's body, (b) obtaining a video image of internal body tissues inside the patient's body via the endoscopic instrument, (c) transmitting, over a telecommunications link, a video signal encoding the video image to a remote location beyond a range of direct manual contact with the patient's body, (d) receiving actuator control signals from the remote location via the telecommunications link, (e) inserting a surgical instrument into the patient's body, and (f) automatically operating the surgical instrument in response to the received actuator control signals.

It is to be noted that the endoscopic instrument may take the form of a traditional flexible endoscope or a rigid laparoscope. In the latter case, as in all laparoscopic surgery, a body cavity of the patient is subject to pressurized air to inflate the cavity and permit manipulation of instruments so that they can move around unimpeded inside the patient.

A surgical system, in accordance with the present invention, comprises an endoscopic instrument, a camera on the endoscopic instrument for obtaining video images of internal body tissues inside a patient's body via the endoscopic instrument, and a transmitter operatively connected to the camera for transmitting, over a telecommunications link to a remote location beyond a range of direct manual contact with the patient's body, a video signal encoding the video image. A receiver is provided for receiving actuator control signals from the remote location via the telecommunications link. The receiver feeds the signals to a robot actuator mechanism for controlling that mechanism to operate a surgical instrument insertable into the patient's body.

A system and method in accordance with the present invention enables operations to be performed by leading surgeons who are not present in the operating room. Such surgeons may reside at great distances from where the operations are to be performed and may be unable to travel to reach the locations of the operations. Because travel time can virtually be eliminated, leading surgeons can perform a greater number of operations all over the globe.

BRIEF DESCRIPTION OF THE DRAWING

The sole FIGURE of the drawing is a diagram of a remotely controlled operating system in accordance with the present invention.

DETAILED DESCRIPTION

As illustrated in the drawing FIGURE, a patient P undergoing laparoscopic surgery, for example, removal of a gall bladder GB, has an internal body cavity C pressurized with air to distend the abdominal wall AW. The abdominal wall is pierced with a trocar (not shown) and a plurality of hollow tubes 12 and 14 are inserted through the abdominal wall to provide passage for the operating instruments. One such instrument is an endoscopic type device, namely, a laparoscope 16 which includes an optical fiber (not illustrated) for delivering optical radiation OR from a light source or control component 18 to the surgical site. Another instrument takes the form of a forceps instrument 20 or other device for manipulating and/or severing internal body tissues such as gall bladder GB.

Forceps instrument 20 includes a pair of forceps jaws 21 whose position inside body cavity C is controlled by a computer 22 via a two-axis rotary drive 24 and a translatory drive 26. Rotary drive 24 is operatively connected to tube 14 for pivoting the tube at its point of penetration through abdominal wall about two axes of rotation. In response to signals from computer 22, translatory drive 26 slides forceps instrument 20 longitudinally through tube 14.

The orientation of forceps jaws 21 with respect to tube 14 is controlled by computer 22 via a one-axis rotary drive 28, while forceps jaws 21 are alternately opened and closed by an actuation mechanism 30 in response to control signals from computer 22.

The position of a distal tip of laparoscope 16 inside body cavity C is controlled by computer 22 via a two-axis rotary drive 32 mechanically linked to tube 12 and a translatory drive 34 operatively coupled with laparoscope 16. Translatory drive 34 varies the degree of insertion of laparoscope 16 through tube 12, while rotary drive 32 swings tube 12 about two axes of rotation.

The intensity and/or the hue of optical radiation OR is controlled by computer 22 via light source or control component 18. In addition, in the event that laparoscope 16 is flexible, the curvature of the distal end portion of the laparoscope is modifiable by computer 22 via a bend control component 36.

Laparoscope 16 incorporates a charge coupled device (not illustrated) for converting optical incoming radiation, reflected from internal body tissues inside cavity C, to a video signal. That video signal, encoding a video image, is transmitted from laparoscope 16 to a transmitter 38 and optionally to computer 22.

Transmitter 38 in turn transmits the video signal over a telecommunications link 40 to a remote receiver 42 which relays the video signal to another computer 44. Computer 44 uses the incoming video signal to display on a monitor 46 an image of the internal body tissues of patient P.

Connected to computer 44 are at least two sets of input devices 48 and 50 operated by a surgeon to remotely control a surgical procedure. More specifically, input device 48 includes a joy stick 52 for controlling the operation of rotary drive 32, a slide switch 54 for controlling the operation of translatory drive 34, another slide switch 56 for controlling light source or control component 18 to modify light intensity, and a dial or knob 58 for controlling bend control component 36 to change the angle of inclination of the distal end portion of laparoscope 16.

Input device 50 includes a joy stick 60 for controlling the operation of rotary drive 24, a dial or knob 62 for controlling rotary drive 28, a slide switch 64 for controlling translatory drive 26, and another slide switch 66 for controlling instrument actuator 30.

Signals from input devices 48 and 50 are encoded by computer 44 and sent to computer 22 via a transmitter 68, telecommunications link 40, and a receiver 70. Computer 22 then uses the incoming signals to provide control signals to the various drives and other components at the site of the surgery.

It is to be understood, of course, that surgeons and other personnel are present in the operating room at the time of surgery to oversee and supervise the proper operation of the equipment. These personnel may communicate with the remote surgeon via computers 22 and 44 and telecommunications link 40 and/or through other telecommunications or electromagnetic signaling linkages such as the telephone network. To facilitate local supervision, computer 22 is connected to a local monitor (not shown) for displaying the video images garnished by laparoscope 16 and, for example, for displaying alphanumeric codes indicating the positions and operating statuses of the instruments, e.g., light source or control component 18 and forceps instrument 20. Such information may also be transmitted by computer 22 to computer 44 over transmitter 38, link 40 and receiver 42 and displayed on monitor 46. Other parameters regarding the condition of patient P, such as temperature, heart rate, oxygen consumption, brain wave activity, and blood sugar level, may also be automatically sensed, encoded and transmitted to remote computer 44 for providing the lead surgeon in real time with all information necessary for performing the surgery successfully.

Although the invention has been described in terms of particular embodiments and applications, one of ordinary skill in the art, in light of this teaching, can generate additional embodiments and modifications without departing from the spirit of or exceeding the scope of the claimed invention. For example, other kinds of optically guided surgery may be performed from a remote location via the computer aided automation of the instant invention, Accordingly, it is to be understood that the drawings and descriptions herein are profferred by way of example to facilitate comprehension of the invention and should not be construed to limit the scope thereof.

What is claimed is:

1. A surgical method, comprising the steps of:
   inserting an endoscopic instrument into a patient's body;
   obtaining a video image of internal body tissues inside said patient's body via said endoscopic instrument;
   transmitting, over an electromagnetic signaling link, a video signal encoding said video image to a remote location beyond a range of direct manual contact with said patient's body and said endoscopic instrument;
   receiving actuator control signals from said remote location via said electromagnetic signaling link;
   inserting into the patient's body a surgical instrument movable relative to the patient's body and said endoscopic instrument; and
   automatically operating said surgical instrument in response to the received actuator control signals to effect a surgical operation on said internal body tissues.

2. The method recited in claim 1 wherein said endoscopic instrument includes a laparoscope, further comprising the step of inflating a body cavity of the patient.

3. The method recited in claim 1, further comprising the steps of receiving additional control signals from said remote location via said electromagnetic signaling link and automatically operating said endoscopic instrument in response to said additional signals.

4. The method recited in claim 3 wherein said step of automatically operating said endoscopic instrument includes the step of operating said endoscopic instrument to vary said video image.

5. The method recited in claim 4 wherein said step of automatically operating said endoscopic instrument includes the step of mechanically moving said endoscopic instrument with respect to the patient's body, thereby varying said video image.

6. The method recited in claim 1 wherein said step of automatically operating said surgical instrument includes the step of mechanically moving said surgical instrument with respect to the patient's body and with respect to said endoscopic instrument.

7. The method recited in claim 6 wherein said step of mechanically moving said surgical instrument includes the steps of pivoting said surgical instrument with respect to the patient's body and with respect to said endoscopic instrument.

8. The method recited in claim 6 wherein said step of mechanically moving said surgical instrument includes the steps of translating said surgical instrument with respect to the patient's body and with respect to said endoscopic instrument.

9. The method recited in claim 1 wherein said surgical instrument is a laparoscopic instrument partially inserted into the patient separately from said endoscopic instrument.

10. A surgical system comprising:
    an endoscopic instrument;

camera means on said endoscopic instrument for obtaining video images of internal body tissues inside a patient's body via said endoscopic instrument;

transmission means operatively connected to said camera means for transmitting, over an electromagnetic signaling link to a remote location beyond a range of direct manual contact with said patient's body and said endoscopic instrument, a video signal encoding said video image;

receiver means for receiving actuator control signals from said remote location via said electromagnetic signaling link;

a surgical instrument insertable into the patient's body and movable relative to the patient's body and said endoscopic instrument; and robot actuator means operatively connected to said surgical instrument and said receiver means for actuating said surgical instrument in response to the actuator control signals received by said receiver means from said remote location.

11. The system recited in claim 10 wherein said endoscopic instrument includes a laparoscope.

12. The system recited in claim 10, further comprising means for automatically operating said endoscopic instrument in response to additional signals received by said receiver means from said remote location via said electromagnetic signaling link.

13. The system recited in claim 12 wherein said means for automatically operating said endoscopic instrument includes means for automatically operating said endoscopic instrument to vary said video image.

14. The system recited in claim 13 wherein said means for automatically operating said endoscopic instrument includes means for mechanically moving said endoscopic instrument with respect to the patient's body, thereby varying said video image.

15. The system recited in claim 10 wherein said robot actuator means includes means for pivoting said surgical instrument with respect to the patient's body and with respect to said endoscopic instrument.

16. The system recited in claim 10 wherein said robot actuator means includes means for translating said surgical instrument with respect to the patient's body and with respect to said endoscopic instrument.

17. A surgical system comprising:

a trocar sleeve adapted for insertion through a patient's skin surface into an internal body cavity of the patient;

an endoscopic instrument having an at least partially rigid insertion portion, said endoscopic instrument being slidably inserted through said trocar sleeve so that a distal end of said endoscopic instrument is extendible into the internal body cavity of the patient;

camera means on said endoscopic instrument for obtaining video images of internal body tissues inside a patient's body via said endoscopic instrument;

transmission means operatively connected to said camera means for transmitting, over an electromagnetic signaling link to a remote location beyond a range of direct manual contact with said patient's body and said endoscopic instrument, a video signal encoding said video image;

receiver means for receiving actuator control signals from said remote location via said electromagnetic signaling link; and robot actuator means operatively connected to said receiver means and at least one of said endoscopic instrument and said trocar sleeve for automatically pivoting and translating said insertion portion relative to the patient's body in response to the actuator control signals received by said receiver means from said remote location.

18. The system recited in claim 17 wherein said endoscopic instrument includes a laparoscope.

19. The system recited in claim 17, further comprising means for automatically operating said endoscopic instrument in response to said actuator signals received by said receiver means from said remote location via said electromagnetic signaling link.

20. The system recited in claim 19 wherein said means for automatically operating said endoscopic instrument includes means for automatically operating said endoscopic instrument to vary said video image.

* * * * * uNITED STATES PATENT AND TRADEMARK OFFICE
Certificate

Patent No. 5,217,003                      Patented: June 8, 1993

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Peter J. Wilk, New York, NY; and Robert Neil Sudol, Scarsdale, NY.

Signed and Sealed this Thirteenth Day of December 2005.

NICHOLAS D. LUCCHESI
*Supervisory Patent Examiner*
Art Unit 3763